US008883002B2

(12) United States Patent
Murakami et al.

(10) Patent No.: US 8,883,002 B2
(45) Date of Patent: Nov. 11, 2014

(54) SEPARATING AGENT FOR OPTICAL ISOMERS AND SEPARATION COLUMN FOR OPTICAL ISOMERS

(75) Inventors: Tatsushi Murakami, Myoko (JP); Akihiro Nakanishi, Tsukuba (JP); Dieter Lubda, Bensheim (DE); Michael Schulte, Bischofsheim (DE)

(73) Assignees: Daicel Chemical Industries, Ltd., Osaka (JP); Merck Patent GmbH, Darmstadt (DE)

( * ) Notice: Subject to any disclaimer, the term of this patent is extended or adjusted under 35 U.S.C. 154(b) by 989 days.

(21) Appl. No.: 12/979,031

(22) Filed: Dec. 27, 2010

(65) Prior Publication Data

US 2011/0094955 A1    Apr. 28, 2011

Related U.S. Application Data

(60) Division of application No. 11/806,033, filed on May 29, 2007, which is a continuation of application No. PCT/JP2005/021913, filed on Nov. 29, 2005.

(30) Foreign Application Priority Data

Nov. 29, 2004    (JP) ................................ 2004-343683

(51) Int. Cl.
*B01J 20/29* (2006.01)
*G01N 30/52* (2006.01)
*B01J 20/32* (2006.01)
*B01J 20/286* (2006.01)

(52) U.S. Cl.
CPC .......... *G01N 30/52* (2013.01); *G01N 2030/528* (2013.01); *B01J 20/3272* (2013.01); *B01J 20/29* (2013.01); *B01J 20/286* (2013.01)
USPC ...... 210/198.2; 210/635; 210/656; 210/502.1

(58) Field of Classification Search
CPC ...... B01J 20/286; B01J 20/29; B01J 20/3272; G01N 30/52; G01N 2030/528
USPC ............................ 210/635, 656, 198.2, 502.1
See application file for complete search history.

(56) References Cited

U.S. PATENT DOCUMENTS

| 6,398,962 | B1 | 6/2002 | Cabrera et al. |
| 6,562,744 | B1 | 5/2003 | Nakanishi et al. |
| 2006/0189796 | A1 | 8/2006 | Okamoto et al. |

FOREIGN PATENT DOCUMENTS

| DE | 197 26 152 A1 | 12/1998 |
| DE | 198 01 575 A1 | 7/1999 |
| JP | 57-150432 A | 9/1982 |
| JP | 63-307829 A | 12/1988 |
| JP | 6-265534 A | 9/1994 |
| JP | 11-292528 A | 10/1999 |
| JP | 2000-515627 A | 11/2000 |
| JP | 2002-505005 A | 2/2002 |
| JP | 2002-148247 A | 5/2002 |
| WO | WO 95/03256 A1 | 2/1995 |
| WO | WO 95/23125 A1 | 8/1995 |
| WO | WO 03/072640 A2 | 9/2003 |
| WO | WO 2004/095018 A1 | 11/2004 |

OTHER PUBLICATIONS

Chinese Office Action issued Nov. 27, 2009 in corresponding Chinese Application No. 200580047438.4.
DE-19726152 Al: col. 1, Line 68—col. 3, Line 17, Partial Translation.
Search Report Dated Oct. 20, 2009 from European Patent Application No. 05 811 734.2.
U.S. PTO Translation 2010-2285 of Cabrera (DE 19801575).
U.S. PTO Translation 2010-2286 of Cabera (DE 19726152).
Yoshio Okamoto et al., J. Am. Chem. Soc. 1984, vol. 106, 5357-5359.

*Primary Examiner* — Ernst G Therkorn
(74) *Attorney, Agent, or Firm* — Birch, Stewart, Kolasch & Birch, LLP

(57) ABSTRACT

This invention provides a separating agent for optical isomers, which has high asymmetry recognition ability and can be used particularly at a high flow rate when used for the separation of the optical isomers, and a separation column for optical isomers having the same. This invention provides: a separating agent for optical isomers which is used for separation of optical isomers in a sample comprising the optical isomers, which is comprising a monolithic inorganic type carrier having a meso pore formed on an inner wall surface of a specific macropore, and a polysaccharide or a polysaccharide derivative supported on the monolithic inorganic type carrier, wherein the meso pore has a pore size of 6 to 100 nm; and a separation column for optical isomers in which the separating agent for optical isomers is held in a column tube.

6 Claims, No Drawings

US 8,883,002 B2

SEPARATING AGENT FOR OPTICAL ISOMERS AND SEPARATION COLUMN FOR OPTICAL ISOMERS

CROSS REFERENCE

The present application is a divisional application based upon application Ser. No. 11/806,033, filed on May 29, 2007, to which priority is claimed under 35 U.S.C. §120. Application Ser. No. 11/806,033 is a continuation of international application PCT/JP2005/021913, filed on Nov. 29, 2005, which designated the United States, to which priority is also claimed under 35 U.S.C. §120. This application claims priority under 35 U.S.C. §119(a) to patent application no. 2004-343683 filed in Japan on Nov. 29, 2004. The contents of each of the foregoing applications is hereby incorporated by reference.

BACKGROUND OF THE INVENTION

1. Field of the Invention

The present invention relates to a separation column for optical isomers, and more particularly to a separation column for optical isomers used for separation of the optical isomers by chromatography. In particular, the invention relates to a separation column for optical isomers which efficiently separates a broad range of compounds in the separation of pharmaceuticals, foods, agricultural chemicals and perfumes.

2. Description of Related Art

Optical isomers having a relationship of a real image and a mirror image have the same physical and chemical properties such as a boiling point, a melting point, and solubility, but often show differences in interactions for a living matter such as a bioactive including taste and odor. In particular, in the field of pharmaceutical preparations, there are significant differences in an effect of a medicine and toxicity between the two optical isomers. Therefore, in the Guideline for the Production of Pharmaceuticals, the Ministry of Health, Labor and Welfare describes that "when a drug is a racemic modification, it is desirable to preliminarily study absorption, distribution, metabolism and movement of excretion for each isomer".

As stated above, optical isomers have completely the same physical and chemical properties such as a boiling point, a melting point, and solubility, therefore, each optical isomer could not be separated by classical, ordinary separation means and it was not possible to study on interaction of an individual optical isomer with the living matter. Thus, energetic studies have been made on techniques for separating optical isomers in order to analyze a wide variety of optical isomers conveniently with high precision.

And as a separation technique that meets these requirements, an optical resolution method by high performance liquid chromatography (HPLC), in particular an optical resolution method by separation columns for optical isomers for HPLC has progressed. As the separation columns for optical isomers referred to herein, a chiral stationary phase composed of an asymmetry recognition agent itself or a chiral stationary phase composed of an asymmetry recognition agent supported on a suitable carrier is used.

Known examples of the asymmetry recognition agent include optical active triphenylmethyl polymethacrylate (see e.g., JP 57-150432 A), cellulose, amylose derivatives (see, e.g., Okamoto Y., Kawashima M., and Hatada K., J. Am. Chem. Soc., 106:5357, 1984), and ovomucoid which is protein (see e.g., JP 63-307829 A).

Meanwhile, in a column configured by filling a particulate inorganic type filler such as silica gel into a tube, resistance to flow of fluid is first increased and thus pressure drop is increased. Consequently, a flow per unit time period is reduced, and a long time is required for the separation when used as chromatography. Additionally, since the flow per unit time period is small, productivity per unit time period is small, and generally it has not been adequate to mass production of separation subjects.

As a column to dissolve this drawback, a column made up of a monolithic inorganic type porous body (see e.g., JP 6-265534 A) has been known. As a method of producing such a column made up of an monolithic inorganic type porous body, the method of sealing a space between the inorganic type porous body and a column tube by softening plastic or glass with heat has been known (see e.g., JP 2002-505005 A). Moreover, a separation column for optical isomers where cyclodextrin as an asymmetry recognition agent is chemically bound to a monolithic inorganic type porous body has been known (see e.g., JP 2000-515627 A).

However, in the manufacture of currently known separation columns for optical isomers using the monolithic inorganic type porous body, there are some cases where reactivity of the monolithic inorganic type porous body with the asymmetry recognition agent is low. Besides, there are some cases where the asymmetry recognition agent chemically bound to the monolithic inorganic type porous body is decomposed at the manufacture of columns. Depending on conditions of the column manufacture, the asymmetry recognition agent used is sometimes limited and there are some cases where the column cannot be applied to a broad range of optical isomers. There have been problems described above in the manufacture of the separation columns for optical isomers, and tasks still remain for practical application thereof.

SUMMARY OF THE INVENTION

It is an object of the invention to provide a separating agent for optical isomers which has high asymmetry recognition ability and can be used particularly at a high flow rate when used for the separation of the optical isomers, and a separation column for optical isomers having the same.

As a result of an intensive study on a separating agent for optical isomers having characteristic asymmetry recognition ability, the inventors of the present invention have accomplished the present invention.

That is, the present invention is a separating agent for optical isomers which is used for separation of optical isomers in a sample comprising the optical isomers, which is comprising a monolithic inorganic type carrier, and at least one of a polysaccharide and a polysaccharide derivative supported on the monolithic inorganic type carrier, wherein: the monolithic inorganic type carrier comprises a porous body in which channels are formed through connection of cavities from one end to the other end of the monolithic inorganic type carrier; the cavities each comprise a macropore and a meso pore formed on an inner wall surface of the macropore; and the meso pore has a pore size of 6 to 100 nm.

Further, the present invention provides a separation column for optical isomers, comprising: a column tube; and the above-mentioned separating agent for optical isomers which is held in the column tube.

According to the present invention, a monolithic inorganic type carrier having a specific meso pore formed on the inner wall surface of the macropore is used, and at least one of a polysaccharide and a polysaccharide derivative capable of separating optical isomers is supported on the monolithic inorganic type carrier. Thus, the present invention provides a separating agent for optical isomers having high asymmetry identifying ability and a separation column for optical isomers which can be used in separation, analysis, and fractionation of a wide variety of optical isomers at a high flow rate.

DETAILED DESCRIPTION OF THE PREFERRED EMBODIMENT

Hereinafter, an embodiment of the invention is illustrated in detail.

The separating agent for optical isomers of the invention has a porous monolithic inorganic type carrier and polysaccharide or a derivative thereof supported on this monolithic inorganic type carrier. In the invention, the polysaccharide or the derivative thereof may be directly supported on the monolithic inorganic type carrier, or may be supported through another compound which is appropriate.

The monolithic inorganic type carrier is generally a cylindrical inorganic type porous body which may be held in a column tube and has a flow path formed through connection of cavities from one end to the other end of the monolithic inorganic type carrier. That is, the monolithic inorganic type carrier is different from a particulate carrier filled in the column tube.

The monolithic inorganic type carrier preferably contains silica as a major ingredient, but may be comprised of another inorganic material and may contain a small amount of an organic material. When silica is the major ingredient, it is desirable that surface treatment is given to the monolithic inorganic type carrier in order to exclude an effect of a residual silanol group, but there is no problem even if the surface treatment is not given.

The monolithic inorganic type carrier may employ a known inorganic type carrier or an improved article thereof. Examples thereof include: a porous shaped body described in JP 2000-515627 A; a monolithic adsorbent described in JP 2002-505005 A; and an inorganic porous column described in JP H06-265534 A.

The monolithic inorganic type carrier can be made by known methods and methods according thereto. The monolithic inorganic type carrier can be manufactured by, for example, a sol-gel method where a structure with a solvent rich phase which becomes a huge void is caused by using metal alkoxide as a starting material and adding an appropriate coexisting substance such as a polymer such as polyoxyethylene which dissolves in a solvent to the material as described in JP 7-41374 A.

The cavities forming the channels each have a macropore and a meso pore formed on an inner surface wall of the macropore. A pore size of the macropore may be controlled in accordance with a particle size of the coexisting substance, for example. A pore size of the meso pore may be controlled by solidifying a product of the sol-gel method and then immersing the product in an acidic aqueous solution or a basic aqueous solution, for example.

The macropore is not particularly limited so long as the pore forms channels passing through the monolithic inorganic type carrier along a direction of a flow of a mobile phase when the monolithic inorganic type carrier is provided in a flow path of the mobile phase. The channels formed through connecting of the macropores may consist of pores in a straight line or pores continuing in a three dimensional network. The channels preferably consists of the pores continuing in a three dimensional network from the viewpoint of improving separation performance.

Too small a pore size of the macropore may cause difficulties in sufficiently supporting on a monolithic inorganic type carrier a polysaccharide or a polysaccharide derivative for separating optical isomers. Too large a pore size of the macropore may result in insufficient performance of separating optical isomers. From such viewpoints, a pore size of the macropore is preferably 0.5 to 30 µm, more preferably 0.5 to 10 µm, furthermore preferably 1.0 to 6.0 µm, still more preferably 1.0 to 4.5 µm.

Too small a pore size of the meso pore may result in: difficulties in sufficiently supporting on the monolithic inorganic type carrier a polysaccharide or a polysaccharide derivative for separating optical isomers; prevention of optical isomers in a sample from sufficiently approaching a polysaccharide or a polysaccharide derivative; and insufficient separation of optical isomers by a polysaccharide or a polysaccharide derivative. A pore size of the meso pore can be increased to a level (several hundred nm) distinguished from that of the macropore. However, too large a pore size of the meso pore may result in: a reduced effect of surface area expansion by providing the meso pore; a reduced amount of a polysaccharide or a polysaccharide derivative supported on a monolithic inorganic type carrier; and insufficient separation of optical isomers by a polysaccharide or a polysaccharide derivative. From the above viewpoints, a pore size of the meso pore is preferably 6 to 100 nm, more preferably 15 to 80 nm, furthermore preferably 20 to 60 nm, and still more preferably 20 to 50 nm.

The pore size of the macropore can be represented by a value which can represent a substantial pore size of the macropore in the monolithic inorganic type carrier. For example, the pore size of the macropore can be represented by the median of the pore size distribution of the macropore in the monolithic inorganic type carrier. The pore size distribution of the macropore can be measured by using mercury porosimetry or raster electron microscope.

The pore size of the meso pore can be represented by a value which can represent a substantial pore size of the meso pore in the monolithic inorganic type carrier. For example, the pore size of the meso pore can be represented by the median of the pore size distribution of the meso pore in the monolithic inorganic type carrier. The pore size distribution of the meso pore can be measured by using mercury porosimetry, BET method with nitrogen adsorption, or inverse exclusion chromatography (ISEC).

In particular, the monolithic inorganic type carrier has a macropore having a pore size of 0.5 to 10 µm and a meso pore having a pore size of 15 to 80 nm, preferably a macropore having a pore size of 1.0 to 6.0 µm and a meso pore having a pore size of 20 to 60 nm, more preferably a macropore having a pore size of 1.0 to 4.5 µm and a meso pore having a pore size of 20 to 50 nm.

The polysaccharide may be any of synthetic polysaccharide, naturally occurring polysaccharide and naturally occurring modified polysaccharide, and may be any polysaccharide so long as it is optically active, but those with high regularity of binding manner are preferable, and chain-shaped ones are also preferable.

Examples of the polysaccharide include: β-1,4-glucan (cellulose), α-1,4-glucan (amylose or amylopectin), α-1,6-glucan (dextran), β-1,6-glucan (pustulan), β-1,3-glucan (such as curdlan and schizophyllan), α-1,3-glucan, β-1,2-glucan (Crown Gall polysaccharide), β-1,4-galactan, β-1,4-mannan, α-1,6-mannan, β-1,2-fructan (inulin), β-2,6-fructan (levan), β-1,4-xylan, β-1,3-xylan, β-1,4-chitosan, α-1,4-N-acetylchitosan (chitin), pullulan, agarose, and alginic acid. Also, starches containing amylose are included therein.

Of those, it is preferable to use those which can be easily obtained as highly pure polysaccharides such as cellulose, amylose, β-1,4-xylan, β-1,4-chitosan, chitin, β-1,4-mannan, inulin, and curdlan, and more preferably cellulose and amylose.

It is preferred that such a polysaccharide has a number-average degree of polymerization (i.e., the average number of pyranose or furanose rings per molecule) of 5 or more, and more preferably of 10 or more. From the viewpoint of easy handling, it is preferred that the number-average degree of polymerization is 1,000 or less, although the upper limit thereof is not particularly limited. Particularly, it is preferred that a number-average degree of polymerization of polysaccharide is from 50 to 400 in that the polysaccharide or the derivative thereof is supported on the inner wall face of the monolithic inorganic type carrier having meso pores and a sufficient separation effect of the optical isomers is obtained.

The polysaccharide derivative is not particularly limited so long as it is the polysaccharide derivative which can be used for the separation of optical isomers. Such polysaccharide derivatives include, for example, polysaccharide derivatives which contain optical active polysaccharide as a skeleton and where at least a part of a hydroxyl group and an amino group which this polysaccharide has is substituted with a functional group which acts on an optical isomer in a sample.

The functional group is a functional group which acts on the optical isomer in the sample containing the optical isomers which are subject to the separation. Actions of the functional group for the optical isomer cannot be collectively defined because a type of the functional group is different depending on a type of the optical isomers which are subject to the separation, but they are not particularly limited so long as they are the actions sufficient to perform optical resolution of the optical isomers by the polysaccharide derivatives.

Such actions include affinitive interactions such as hydrogen bond, π-π interaction and dipole-dipole interaction of the optical isomer with the functional group, and non-affinitive interaction such as steric hindrance. By such interactions, it is believed that when a pair of the optical isomers gets close to the polysaccharide derivative, a direction of the optical isomer can be arranged without disturbing access of at least one or the optical isomers to the polysaccharide derivative or a higher structure of the polysaccharide derivative itself can be arranged in a shape favorable for asymmetry recognition.

The functional group is selected depending on the type of the optical isomers which are subject to the separation. The functional groups include groups including aromatic groups which are bound to the polysaccharide, for example via ester bond, urethane bond and ether bond and which may have substituents. The aromatic groups include heterocyclic rings and condensed rings. Substituents which the aromatic group may have include, for example, alkyl groups with up to about 8 carbons, halogen, amino groups, and alkoxy groups.

A degree of substitution of the functional group is not particularly limited. The functional group may be substituted with part or all of the hydroxyl groups and amino groups of the polysaccharide, for example. The degree of substitution of the functional group is arbitrarily selected depending on various conditions such as a type of the functional group and a type of the polysaccharide. To be specific, a degree of substitution of the functional group is preferably 50 to 100%, more preferably 80 to 100%. The degree of substitution of the functional group can be measured through elemental analysis, for example.

The polysaccharide derivative can be made by known methods. The polysaccharide derivative can be made, for example, by making a compound capable of reacting with a hydroxyl group or amino group contained in the polysaccharide, which includes the functional group or becomes the functional group by a reaction with the hydroxyl or amino group, to react with the polysaccharide by a dehydration reaction. From the viewpoint of realizing the separation of a broad range of optical isomers, it is particularly preferred that the polysaccharide derivative is a carbamate derivative of polysaccharide or an ester derivative of polysaccharide as described in, for example, WO 95/23125 A1 and the like.

The polysaccharide or the derivative thereof can be supported on the monolithic inorganic type carrier by distilling off a solvent from the monolithic inorganic type carrier filled with a solution of polysaccharide which contains the polysaccharide or the derivative thereof and the solvent, or replacing the solvent with another solvent, or performing both distilling off the solvent and replacing the solvent with the other solvent.

The term "supported" referred to herein includes a direct or indirect physical adsorption of the monolithic inorganic type carrier with the polysaccharide or the derivative thereof, and a direct or indirect chemical bond of the monolithic inorganic type carrier with the polysaccharide or the derivative thereof.

When both distilling off the solvent and replacing the solvent with the other solvent are performed, the solvent may be distilled off to some extent and subsequently the remaining solvent may be replaced with the other solvent, or the solvent may be replaced with the other solvent and subsequently the remaining solvent may be distilled off.

As the solvent (good solvent) used for dissolution of the polysaccharide or the derivative thereof, any organic solvents typically used may be used so long as they can dissolve the polysaccharide or the derivative thereof.

Examples of the solvent include: as ketone based solvents, acetone, ethylmethylketone, and acetophenone; as ester based solvents, ethyl acetate, methyl acetate, propyl acetate, methyl propionate, methyl benzoate, and phenyl acetate; as ether based solvents, tetrahydrofuran, 1,4-dioxane, diethylether, and tert-butylmethylether; as amide based solvents, N,N-dimethylformamide and N,N-dimethylacetamide; as imide based solvents, N,N-dimethylimidazolidinone; as halogen based solvents, chloroform, methylene chloride, carbon tetrachloride, and 1,2-dichloroethane; as hydrocarbon based solvents, pentane, petroleum ether, hexane, heptane, octane, benzene, toluene, xylene, and mesitylene; as urea based solvents, tetramethyl urea; as alcohol based solvents, methanol, ethanol, propanol, and butanol; as acid based solvents, acetic acid, trifluoroacetic acid, formic acid, phenol, and catechol; and as amine based solvents, diethylamine, triethylamine, and pyridine. These solvents may be used alone or in mixture with multiple types.

The other solvent (poor solvent) is not particularly limited so long as it is a solvent which replaces the solvent from the solution of polysaccharides, but is preferably a solvent which replaces in favor of the solvent from the solution of the polysaccharides. As such another solvent, a solvent which is insoluble or poorly soluble for the polysaccharide or the derivative thereof is preferable, and can be appropriately selected from known solvents depending on conditions such as solubility for the polysaccharide or the derivative thereof and compatibility with the above solvent.

Supercritical fluid can be used as a solvent which dissolves the polysaccharide and the derivative thereof. The supercritical fluid referred to herein is referred to fluid at a supercritical temperature and/or pressure at which gas and liquid can coexist or above. As this supercritical fluid, it is preferable to use carbon dioxide, nitrogen monoxide, ammonia, sulfur dioxide, hydrogen halide, hydrogen sulfide, methane, ethane, propane, ethylene, propylene, halogenated hydrocarbon, and the like, and carbon dioxide is more preferable.

An organic solvent can be added to the supercritical fluid. As this organic solvent, it is preferable to use alcohols such as ethanol, methanol and 2-propanol; organic acids such as acetic acid and propionic acid; amines such as diethylamine; aldehydes such as acetaldehyde; and ethers such as tetrahydrofuran and ethyl ether. An addition amount of the organic solvent is preferably from 1 to 50%, more preferably from 1 to 35%, and still preferably from 1 to 20% based on the supercritical fluid.

When filling the solution of polysaccharides into the monolithic inorganic type carrier, a concentration of the solvent is from 1 to 100 parts by mass, preferably from 1 to 50 parts by mass, and more preferably from 1 to 20 parts by mass based on 1 part by mass of the polysaccharide or the derivative thereof.

The monolithic inorganic type carrier having a meso pore of the above-mentioned pore size can support a larger amount of the polysaccharides in the meso pore compared with that of the conventional monolithic inorganic type carrier.

Further, the monolithic inorganic type carrier having a meso pore of the above-mentioned pore size can facilitate transfer of a substance into and out of the meso pore compared with that of the conventional monolithic inorganic type carrier. Thus, the monolithic inorganic type carrier can support a sufficient amount of the polysaccharides on a wall surface of the meso pore even when a solution of the polysaccharides having a relatively high viscosity is used.

The separating agent for optical isomers of the invention can be manufactured by a method including the steps of filling the solution of polysaccharides into the monolithic inorganic type carrier, and at least one of distilling off the solvent from the monolithic inorganic type carrier in which the solution is filled and replacing the solvent with the other solvent in the monolithic inorganic type carrier in which the solution is filled.

The step of filling the solution of polysaccharides into the monolithic inorganic type carrier includes a method of directly immersing the monolithic inorganic type carrier in the solution of polysaccharides and a method of passing the solution of polysaccharides through the monolithic inorganic type carrier with pressure. It is preferred that the step of filling the solution of polysaccharides into the monolithic inorganic type carrier is performed under pressure. The pressure at that time is preferably from 50 to 400 bar, more preferably from 50 to 200 bar. A method of applying pressure to the solution toward the monolithic inorganic type carrier is not particularly limited, and includes the application of pressure by high pressure gas from a bomb or a compressor, and the application of pressure by a pump used in HPLC.

As the step of distilling off the solvent from the monolithic inorganic type carrier in which the solution is filled, an appropriate method is selected depending on the type of the solution. Such a method includes, for example, drying under normal pressure and drying under reduced pressure. In the invention, such methods may be used alone or in combination.

The step of replacing the solvent with another solvent in the monolithic inorganic type carrier in which the solution is filled includes a method of directly immersing the monolithic inorganic type carrier in which the solution is filled in the other solvent and a method of passing the other solvent through the monolithic inorganic type carrier with pressure, similarly to the step of filling the solution of polysaccharides into the monolithic inorganic type carrier.

When the step of filling the solution of polysaccharides into the monolithic inorganic type carrier, and the step of at least one of distilling off the solvent from the monolithic inorganic type carrier in which the solution is filled and replacing the solvent with the other solvent therein are made into one step of supporting the polysaccharide or the derivative thereof on the monolithic inorganic type carrier, the support of the polysaccharide or the derivative thereof on the monolithic inorganic type carrier may be performed at one step or may be repeatedly performed at multiple steps, but it is preferred that it is performed at preferably from 1 to 5 steps, more preferably from 1 to 3 steps, and still preferably 1 step.

The separating agent for optical isomers of the invention may perform stronger fixation of the polysaccharide or the derivative thereof on the monolithic inorganic type carrier by forming further chemical bonds by chemical bonds between the monolithic inorganic type carrier and the polysaccharide or the derivative thereof, chemical bonds between the polysaccharides or the derivatives thereof on the monolithic inorganic type carrier, chemical bonds using a third component, reactions by photo irradiation, irradiation of radioactive rays such as γ-rays, and irradiation of electromagnetic waves such as microwaves to the polysaccharide or the derivative thereof on the monolithic inorganic type carrier, radical reactions, and the like. According to such strong fixation, when used for the separation of the optical isomers, further improvement of availability in industries is anticipated in the separation, analysis and fractionation etc. of the optical isomers.

Examples of a method of fixing the polysaccharide or the derivative thereof on the monolithic inorganic type carrier by the chemical bond include, a method including the steps of binding the monolithic inorganic type carrier to a binder which is fixed on the surface of this monolithic inorganic type carrier by the chemical bond, accreting the polysaccharide or the derivative thereof to the monolithic inorganic type carrier to which the binder is bound, and directly or indirectly binding the accreting polysaccharide or derivative thereof with the binder.

This method may further include the step of introducing substituents into the polysaccharide or the derivative thereof which binds to the binder. In the case of including such a step, it is possible to regulate a substitution ratio of the substituent in the polysaccharide derivative. In the case of including the step, it is also become possible to bind the polysaccharide to the binder and introduce the substituent including the functional group into the polysaccharide which binds to the binder.

The binder is not particularly limited so long as it is a compound which is fixed to the surface of the monolithic inorganic type carrier by the chemical bond and can further chemically bind to the polysaccharide or the derivative thereof. Also, the binder and the polysaccharide or the derivative thereof may be directly bound chemically, or indirectly bound chemically via another compound such as a crosslinking agent. The binder is appropriately selected depending on a composition of the surface of the monolithic inorganic type carrier, and the preferable binders include, for example, organic silicon compounds such as silane coupling agents.

The separation column for optical isomers of the invention has a column tube and the separating agent for optical isomers held in this column tube.

As the column tube, the column tube typically used can be used depending on a use form of the column and a scale of the column.

The separating agent for optical isomers is held in the column tube to become a channel for fluid within the column tube. A method of holding the separating agent for optical isomers in the column tube is not particularly limited so long as it is the method capable of sealing space between an inner wall face of the column tube and a surface opposite thereto of the separating agent for optical isomers. Known methods can be used in which the monolithic inorganic type carrier is held in the column tube. As such a method, for example, as disclosed in JP 2002-505005 A, it is possible to use a method of sealing the space between the inner wall face of the column tube and the surface opposite thereto of the monolithic inorganic type carrier by plastic, and the like.

The separation column for optical isomers of the invention may be manufactured by holding the separating agent for optical isomers in the column tube, or may be manufactured by supporting the polysaccharide or the derivative thereof by the aforementioned steps on the monolithic inorganic type carrier of the column having the monolithic inorganic type carrier held in the column tube to become a channel of fluid within the column tube. The method of supporting the polysaccharide or the derivative thereof in the column having the monolithic inorganic type carrier is preferable from the viewpoint of prevention of decomposition of the supported polysaccharide or derivative thereof, ease of the manufacture, and the like.

The separation column for optical isomers of the invention is generally used for chromatography methods such as gas chromatography, high-performance liquid chromatography, supercritical chromatography, thin layer chromatography, and capillary electrophoresis. In particular, it is preferable to apply the separation column to the high-performance liquid chromatography method.

Without further elaboration, it is believed that one skilled in the art can, using the preceding description, utilize the present invention to its fullest extent. The preferred specific embodiments and examples are, therefore, to be construed as merely illustrative, and not limitative of the disclosure in any way whatsoever.

The entire disclosures of all applications, patents, and publications cited above and below, and of corresponding application Japanese JP2004-343683, filed Nov. 29, 2004, are hereby incorporated by reference.

EXAMPLES

The present invention is described below in more detail based on examples, but the invention is not limited to the following examples.

Example 1

Production of a monolithic inorganic type porous body column supporting amylose tris(3,5-dimethylphenylcarbamate)

(1) Synthesis of amylose tris(3,5-dimethylphenylcarbamate)

In a nitrogen atmosphere, 10 g of amylose and 68.1 g (2.5 equivalents with respect to all of hydroxyl groups of amylose) of 3,5-dimethylphenyl isocyanate in 300 mL of dry pyridine were stirred under heating at 100° C. for 48 hours, and the whole was poured in to 3 L of methanol. A separated solid was filtered and collected on a glass filter, washed with methanol several times, and dried in a vacuum. As a result, 34 g of a yellowish white solid was obtained.

(2) Supporting of amylose tris(3,5-dimethylphenylcarbamate) on a monolithic inorganic type porous body Amylose tris(3,5-dimethylphenylcarbamate) synthesized in (1) was dissolved in ethyl acetate. A concentration of the solution was 75 mg/mL.

A monolithic inorganic porous body, which has a macropore having a pore size of 1.9 μm and a meso pore having a pore size of 25 nm formed on an inner wall surface of the macropore, was used as a monolithic inorganic type porous body. The solution was injected into a monolithic inorganic type porous body column from an end part using a pump for HPLC at a pressure within a maximum pressure of 200 bar. The monolithic inorganic type porous body column has the monolithic inorganic porous body held in a column tube having a length of 50 mm and an inner diameter of 4.6 mm. The injection of the solution was stopped after the solution containing the polysaccharide derivative was observed from a tip part of the inorganic type porous body column (end part of the inorganic type porous body column opposite to the end part connecting with the pump). Both ends of the inorganic type porous body column were opened, and the inorganic type porous body column was dried under normal temperature and normal pressure for about 1 week and then dried under reduced pressure for 4 hours. A weight of the inorganic type porous body column was measured before and after drying to determine an end point of a drying step. As described above, an inorganic type porous body column supporting amylose tris(3,5-dimethylphenylcarbamate) was produced.

Example 2

An inorganic type porous body column supporting amylose tris(3,5-dimethylphenylcarbamate) was produced in the same manner as that in Example 1 except that a monolithic inorganic type porous body column holding a monolithic porous body, which has a macropore having a pore size of 4.5 μm and a meso pore having a pore size of 23 nm, in the column tube, was used in place of the monolithic inorganic type porous body column used in Example 1.

Example 3

An inorganic type porous body column supporting amylose tris(3,5-dimethylphenylcarbamate) was produced in the same manner as that in Example 1 except that a monolithic inorganic type porous body column holding a monolithic porous body, which has a macropore having a pore size of 6.0 μm and a meso pore having a pore size of 24.4 nm, in the column tube, was used in place of the monolithic inorganic type porous body column used in Example 1.

Comparative Example 1

An inorganic type porous body column supporting amylose tris(3,5-dimethylphenylcarbamate) was produced in the same manner as that in Example 1 except that a monolithic inorganic type porous body column holding a monolithic porous body, which has a macropore having a pore size of 1.8 μm and a meso pore having a pore size of 10.9 nm, in the column tube, was used in place of the monolithic inorganic type porous body column used in Example 1.

Comparative Example 2

An inorganic type porous body column supporting amylose tris(3,5-dimethylphenylcarbamate) was produced in the same manner as that in Example 1 except that a monolithic inorganic type porous body column holding a monolithic porous body, which has a macropore having a pore size of 4.5 µm and a meso pore having a pore size of 10.2 nm, in the column tube, was used in place of the monolithic inorganic type porous body column used in Example 1.

Comparative Example 3

An inorganic type porous body column supporting amylose tris(3,5-dimethylphenylcarbamate) was produced in the same manner as that in Example 1 except that a monolithic inorganic type porous body column holding a monolithic porous body, which has a macropore having a pore size of 5.74 µm and a meso pore having a pore size of 10.0 nm, in the column tube, was used in place of the monolithic inorganic type porous body column used in Example 1.

<Measurement and Evaluation>

The inorganic type porous body columns produced in Examples 1 to 3 and the inorganic type porous body columns produced in Comparative Examples 1 to 3 were each used for separation of optical isomers shown in Table 1 by liquid chromatography. A retention time of each of the optical isomers in each of the columns was measured, to thereby determine a separation factor α and the number of theoretical plates for each of the columns. Table 1 shows the separation factor α, and Table 2 shows the number of theoretical plates.

TABLE 1

| Racemic modification | Structural formula | Separation factor α (—) | | | | | |
|---|---|---|---|---|---|---|---|
| | | Example 1 | Example 2 | Example 3 | Comparative example 1 | Comparative example 2 | Comparative example 3 |
| t-SO | (epoxide with two Ph groups) | 3.27 | 3.40 | 3.28 | 3.00 | 2.95 | 2.80 |
| Bz | Ph—CH(OH)—C(=O)—Ph | 1.32 | 1.29 | 1.30 | 1.24 | 1.21 | 1.17 |
| TR-base | (dimethyl dibenzodiazocine) | 1.29 | 1.28 | 1.28 | 1.14 | 1.12 | 1.00 |
| TFAE | (anthracenyl-CH(OH)-CF$_3$) | 1.28 | 1.21 | 1.21 | 1.11 | 1.00 | 1.00 |
| TrOH | Ph$_3$C—CH(OH)—Ph | 2.28 | 2.25 | 2.28 | 2.28 | 2.19 | 2.22 |
| Biph | (2,2'-dihydroxy-6,6'-dimethylbiphenyl) | 2.29 | 2.33 | 2.30 | 2.24 | 2.26 | 2.23 |

TABLE 2

| | Amount of supported polymer | Pore size of macropore | Pore size of meso pore | Number of theoretical plates N (—) | | | | | |
|---|---|---|---|---|---|---|---|---|---|
| | | | | t-SO | | Biph | | TrOH | |
| | (mg) | (µm) | (nm) | $N_1$ | $N_2$ | $N_1$ | $N_2$ | $N_1$ | $N_2$ |
| Example 1 | 110.3 | 1.9 | 25 | 2491 | 1738 | 1234 | 1077 | 1255 | 1137 |
| Example 2 | 105.2 | 4.5 | 23 | 1616 | 1119 | 565 | 439 | 414 | 357 |
| Example 3 | 104.8 | 6.0 | 24.4 | 1020 | 476 | 285 | 186 | 189 | 145 |
| Comparative example 1 | 116.7 | 1.8 | 10.9 | 2063 | 1471 | 1051 | 763 | 885 | 752 |

TABLE 2-continued

|  | Amount of supported polymer (mg) | Pore size of macropore (μm) | Pore size of meso pore (nm) | Number of theoretical plates N (—) | | | | | |
|---|---|---|---|---|---|---|---|---|---|
|  |  |  |  | t-SO | | Biph | | TrOH | |
|  |  |  |  | $N_1$ | $N_2$ | $N_1$ | $N_2$ | $N_1$ | $N_2$ |
| Comparative example 2 | 107.4 | 4.5 | 10.2 | 1178 | 688 | 414 | 301 | 263 | 233 |
| Comparative example 3 | 100.1 | 5.74 | 10.0 | 654 | 287 | 170 | 111 | 109 | 77 |

The separation factor α in Table 1 is determined by the following equation (1). In the equation (1), $k_1'$ represents a capacity ratio of an optical isomer eluted faster among the separated optical isomers, and $k_2'$ represents a capacity ratio of an optical isomer eluted slower among the separated optical isomers.

[Formula 1]

$$\text{separation factor } (\alpha) = k_2'/k_1' \quad (1)$$

The capacity ratio $k_r'$ is determined by the following equation (2). In the equation (2), $t_r$ represents a retention time of an optical isomer, and $t_0$ represents an elution time of tri-tert-butylbenzene.

[Formula 2]

$$\text{capacity ratio } (k_r') = (t_r - t_0)/t_0 \quad (2)$$

The number of theoretical plates N in Table 2 is determined by the following equation (3). In the equation (3), $W_{0.5}$ represents a peak width at half height. The peak width W refers to a distance (time) between cross points of tangent lines drawn at inflection points of the peak on both sides of the peak, and a base line.

[Formula 3]

$$\text{number of theoretical plates } (N) = 5.5 \times (t_r/W_{0.5})^2 \quad (3)$$

An amount of the polymer supported in Table 2 refers to a difference (mg) between a mass of the inorganic type porous body column having a polymer supported thereon and a mass of the inorganic type porous body column not having the polymer supported thereon.

Tables 1 and 2 clearly show that the inorganic type porous body column produced in each of Examples exhibits better performance as a separation column for optical isomers compared with the inorganic type porous body column produced in each of Comparative Examples.

What is claimed is:

1. A separating agent for optical isomers which is used for separation of optical isomers in a sample comprising the optical isomers, which separating agent comprises
    a monolithic inorganic type carrier, and
    at least one of a cellulose and a cellulose derivative supported on the monolithic inorganic type carrier, wherein:
    the monolithic inorganic type carrier comprises a porous body in which channels are formed through connection of cavities from one end to the other end of the monolithic inorganic type carrier;
    the cavities each comprise a macropore and a meso pore formed on an inner wall surface of the macropore;
    the macropore has a pore size of 0.5 to 30 μm; and
    the meso pore has a pore size of 23 to 25 nm.

2. The separating agent for optical isomers according to claim 1, wherein the macropore has a pore size of 0.5 to 10 μm.

3. The separating agent for optical isomers according to claim 2, wherein the macropore has a pore size of 1.0 to 6.0 μm.

4. The separating agent for optical isomers according to claim 1, wherein the monolithic inorganic type carrier is mainly composed of silica.

5. The separating agent for optical isomers according to claim 1, wherein the cellulose derivative is one of an ester derivative of cellulose and a carbamate derivative of cellulose.

6. A separation column for optical isomers comprising a column tube and the separating agent for optical isomers according to claim 1 or 2 which is held in the column tube.

* * * * *